Figure 1:
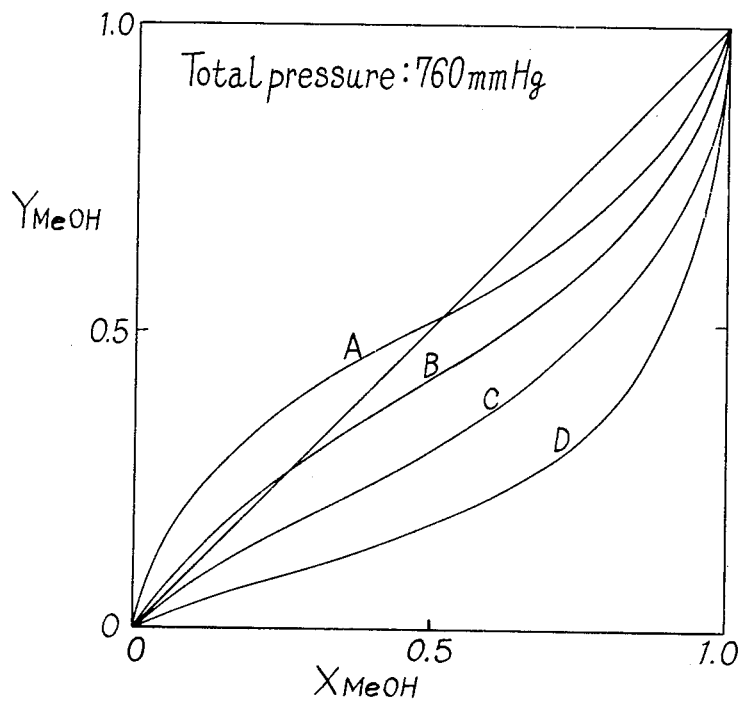

United States Patent

Sato et al.

[11] 3,957,880
[45] May 18, 1976

[54] EXTRACTIVE DISTILLATION OF A METHACROLEIN EFFLUENT

[75] Inventors: Ryozi Sato; Takanori Musha; Yoshio Ito, all of Takaoka, Japan

[73] Assignee: Nippon Zeon Co., Ltd., Tokyo, Japan

[22] Filed: Jan. 3, 1974

[21] Appl. No.: 430,403

[30] Foreign Application Priority Data
Jan. 6, 1973   Japan.................................. 48-4819

[52] U.S. Cl............................. 260/604 HF; 203/42; 203/78; 203/79
[51] Int. Cl.²........................................ C07C 45/02
[58] Field of Search.................. 260/601 R, 604 HF; 203/42, 95–96, 84, 85, 78, 79

[56] References Cited
UNITED STATES PATENTS

| | | | |
|---|---|---|---|
| 2,347,636 | 4/1944 | Spence et al..................... | 260/601 R |
| 2,514,966 | 7/1950 | Pierotti et al........................ | 203/76 |
| 2,606,933 | 8/1952 | Cole et al........................ | 260/601 R |
| 3,098,798 | 7/1963 | Marks................................... | 203/64 |
| 3,162,514 | 12/1964 | Roelen et al..................... | 260/601 R |

FOREIGN PATENTS OR APPLICATIONS
2,110,031   9/1971   Germany.......................... 260/601 R OTHER PUBLICATIONS
Techniques of Organic Chemistry, (pp. 338 & 339), Vol. IV, Distillation – Weissberger, Interscience Publ. Inc., N.Y., 1951.

Primary Examiner—Norman Yudkoff
Assistant Examiner—Frank Sever
Attorney, Agent, or Firm—Toren, McGeady and Stanger

[57] ABSTRACT

Methacrolein is recovered from a crude gaseous mixture in a process comprising the steps of first absorbing the methacrolein from the mixture with a selective solvent to form a liquid mixture and thereafter subjecting the thus formed liquid mixture to an extractive distillation with water.

9 Claims, 2 Drawing Figures

$Y_{MeOH} = \dfrac{y_{MeOH}}{y_{MeOH} + y_{MAL}}$ : Mole fraction of MeOH component in vapor excepting H₂O component $X_{MeOH} = \dfrac{x_{MeOH}}{x_{MeOH} + x_{MAL}}$ : Mole fraction of MAL component in liquid excepting H₂O component A :  $X_{H_2O} = 0$ (MeOH-MAL binary system)

B :  $X_{H_2O} = 0.2$

C :  $X_{H_2O} = 0.5$

D :  $X_{H_2O} = 0.8$

\* MeOH = methyl alcohol
 MAL = methacrolein

EXTRACTIVE DISTILLATION OF A METHACROLEIN EFFLUENT

This invention relates to a process for separating methacrolein from a gaseous mixture containing methacrolein.

Particularly, the present invention provides an advantageous process applicable to the separation of methacrolein from a reaction mixture obtained by the vapor phase catalytic oxidation of isobutylene or an isobutylene-containing hydrocarbon mixture, e.g. a $C_4$ hydrocarbon mixture composed mainly of isobutylene. Further, the process of the present invention is applicable also to the recovery of unreacted methacrolein from a reaction mixture resulting from the vapor phase catalytic oxidation of methacrolein to produce methacrylic acid.

Recently, processes for producing methacrolein and methacrylic acid, which are extremely useful compounds, have been studied and developed. For example, isobutylene, an isobutylene-containing hydrocarbon mixture, e.g. a $C_4$ hydrocarbon mixture composed mainly of isobutylene, or methacrolein is mixed with oxygen, nitrogen and steam, and the resulting mixture is oxidized at an elevated temperature, e.g. 350° to 550°C., in the presence of a catalyst to produce the desired methacrolein or methacrylic acid. In tis case, however, the reaction mixture comprises, in addition to methacrolein or methacrylic acid, unreacted isobutylene or unreacted methacrolein, unreacted oxygen and large amounts of nitrogen and steam, and by-products such as $C_1$-$C_4$ aldehydes, fatty acids, ketones, carbon dioxide and carbon monoxide.

A typical process for separating unsaturated aldehydes from such (gaseous) reaction mixture as mentioned above would be, for example, the process disclosed in U.S. Pat. No. 2,514,966 which is concerned with the separation of acrolein. The process of said Unites States patent is essentially carried out by scrubbing an acrolein-containing gaseous mixture with a large amount of water under a high pressure to form an aqueous solution containing about 2% by weight of acrolein, and then subjecting the said aqueous acrolein solution to stripping, rectification and extractive distillation to separate the acrolein. This process, however, not only has many such disadvantages as mentioned below when applied to the separation of acrolein, but also is quite unsatisfactory from the industrial standpoint as a process for the separation of methacrolein in place of acrolein. While the reasons why such separation process is disadvantageous are disclosed in U.S. Pat. No. 2,606,932, the reasons will be mentioned in more detail below.

A disadvantage of said process lies in that an extremely large amount of water should be used under a high pressure at the time of absorbing acrolein from the gaseous reaction mixture. This is because acrolein is inherently low in water-solubility (21.4% by weight at 20°C.). In addition, so far as water is used as the absorbing solvent, it is impossible to increase the acrolein-absorbing ability of the solvent by maintaining the system at such a low temperature as below 0°C. for example. Accordingly, the efficiency of acrolein absorption should necessarily be enhanced by maintaining the pressure inside the system as high as possible and by using water in an amount as large as possible. However, the passage of such extraordinarily large amounts of water through such scrubbing zone not only renders difficult the maintenance of relatively constant conditions to attain optimum results, but also the scrubbing column, the subsequent crude acrolein-stripping column and other apparatuses should necessarily be made larger, and this will bring about operational and economical disadvantages. Further, the gaseous mixture is composed mainly of uncondensed gases such as nitrogen used as a diluent and by-produced carbon dioxide and carbon monoxide. Accordingly, when the system is intended to be maintained under such a high pressure as 10 to 18 atm. by compressing the gaseous mixture, particularly in the case where the amount of the gaseous mixture is as large as about several 10,000 cubic meters per hour, it is apparent that the costs for construction of compression apparatuses and the utility cost should necessarily be increased, which will cause industrial and economical disadvantages.

Thus, the water used in the process of the aforesaid patent is essentially not suitable as an absorption solvent for acrolein.

Accordingly, even if water is used as an absorption solvent for methacrolein, the abovementioned disadvantages are not overcome but further increased, since methacrolein is lower in watersolubility (6.1% by weight at 25°C.) than acrolein. Thus, it is apparent that water is not suitable as an absorption solvent for methacrolein.

Another disadvantage of the aforesaid process lies in that at the acrolein separation step, an extractive distillation should be effected at a low temperature (below 35°C.) using water as a solvent in such a large amount as at least equal to about 80% by weight of the aqueous mixture containing acrolein. Particularly, the pressure inside the system is required to be reduced to about 50 mmHg in order to maintain the system at a low temperature. In said extractive distillation, a large amount of water is required to be used for such reason that the acrolein-water system in the extractive distillation zone does not become heterogeneous, and a low temperature (i.e. a low pressure) is required to be employed for such reason that no relative volatility (alpha: $\alpha$) advantageous for separation of acrolein can be attained unless said condition is adopted. According to the said process, however, the utility cost is high since a large amount of water is used. Further, when the distillation is carried out under such a reduced pressure as 50 mmHg. for example, the boiling point of acrolein becomes about −10°C., so that not only the use of ordinary cooling water for the cooling of column top distillate becomes impossible with bringing about an increase in cooling cost, but also the column diameter should necessarily be enlarged, and this will cause an increase in initial installation and labor costs.

Other disadvantages of the aforesaid process are such that many steps such as stripping of crude acrolein, distillation of acetaldehyde and extractive distillation of propionaldehyde are required to be disposed between the acrolein absorption step and the step of recovering purified acrolein by extractive distllation, and that in said steps, acrolein is exposed to temperatures equal to or above the boiling point thereof, and hence tends to be lost due to polymerization or other side-reactions.

As mentioned above, the acrolein separation process proposed by U.S. Pat. No. 2,514,966 have many industrial and economical disadvantages, and it is apparent that the said process cannot be applied satisfactorily to the separation of methacrolein which, like acrolein, is an unsaturated aldehyde.

On the other hand, German Offenlegungsschrift No. 2,110,031 discloses a process for separating methacrolein from a gaseous mixture containing methacrolein which comprises (i) an absorption step: absorbing the methacrolein in the gaseous mixture with an alcohol such as methyl alcohol, (ii) a liquid-liquid extraction step: extracting the methyl alcohol from the resulting solution with water to separate the methacrolein as an extraction residue, and (iii) a recovering and recycling step: recovering by adoption of simple distillation part of methzacrolein remained in the extract obtained in said step (ii) as an azeotrope with methyl alcohol and recycling the said azeotrope to the step (ii), and (iv) an alcohol separation step: distilling the aqueous solution obtained in the above step (iii) to separate the methyl alcohol from the water, the methyl alcohol being recycled to the absorption step (i). It is well known that methacrolein (b.p. 73.5°C.) and methyl alcohol (b.p. 64.65°C.) form an aseotrope (b.p. 58°C.) consisting of 70% by weight of methacrolein and 30% by weight of methyl alcohol. According to the simple distillation adopted in the step (iii), therefore, a methacrolein-rich azeotropic distillate is obtained.

The above-mentioned process, however, is not satisfactory in the following points:

So far as the liquid-liquid extraction is conducted in the step (ii), such additional step as the recovering and recycling step of methacrolein (iii) is necessarily required, whereby the operation becomes troublesome and the separation cost becomes high. Further, in case the gaseous mixture is low in methacrolein concentration and high in gas volume, the absorption solvent methyl alcohol must be used in large quantities. The solution obtained in this case is a methyl alcohol-methacrolein solution containing large quantities of methyl alcohol. In order to extract methyl alcohol with water from the said solution containing large quantities of methyl alcohol thereby to separate methacrolein therefrom (step (ii)), the water should be used in exceedingly large quantities. As the result, the amount of the extraction phase (water-methyl alcohol solution containing remained methacrolein) obtained in the step (ii) necessarily becomes exceedingly large. In the step (iii) for the recovery of methacrolein-rich phase by azeotropic distillation, and in the step (iv) for the separation of methyl alcohol from water by distillation, therefore, there are brought about such burdens as, for example, necessity of making the apparatuses greater in size, increase in overall operating costs due to excessive increase in utility cost, and great increase in operational complexity. Thus, the above-mentioned methacrolein separation process is not satisfactory from the industrial standpoint. From the above, it will be understood that in the said process, the amount of water fed in the liquid-liquid extraction step (ii) should necessarily be made larger with increasing the ratio of methyl alcohol to methacrolein in the solution obtained in the step (i).

As the result of extensive studies on processes for separating methacrolein from methacrolein-containing gaseous mixtures, we have accomplished a separation process which is entirely free from such disadvantages as encountered in the above-mentioned known processes and which is quite advantageous from the industrial and economical standpoint.

That is, we have experimentally found that when a specific amount of water is added to a system comprising a mixture of methacrolein and a completely water-soluble alcohol having 1 to 3 carbon atoms (hereinafter abbreviated, sometimes, to "alcohol") which is selected from the group consisting of methyl alcohol, ethyl alcohol, iso-propyl alcohol and normal-propyl alcohol, the relative volatility (hereinafter abbreviated, sometimes, to $\alpha$) of methacrolein to alcohol increases to a great extent over the whole composition range of the methacroleinalcohol system.

More detailed explanation of the above will be made below.

It is well known that among the abovementioned alcohols, methyl alcohol forms, together with methacrolein, an azeotrope containing 70% by weight of methacrolein, at the boiling point of 58°C. Further, the boiling point of methyl alcohol (64.65°C.) is lower than that of methacrolein (73.5°C.).

In the accompanying drawings,

FIG. 1 illustrates graphically the diagrams of vapor and liquid compositions at constant amount of water for the methacrolein-methyl alcohol system under a total pressure of 760 mmHg. $x_{MAL}$ and $x_{MeOH}$ stand for mole fraction of methacrolein and methanol, respectively, in the liquid methacrolein-methyl alcohol-water ternary components: $y_{MAL}$ and $y_{MeOH}$ stand for mole fraction of methacrolein and methanol, respectively, in the vapor methacrolein-methyl alcohol-water ternary components. The amount of water ($x_{H_2O}$) is represented by the mole fraction of water in a liquid consisting of methyl alcohol, nethacrolein and water, Thus, the curve A is the diagram of the case where no water is added, i.e. the case of a binary system comprising methyl alcohol and methacrolein. The curve A intersects the diagonal line. This indicates that the binary system comprising methyl alcohol and methacrolein forms an azeotrope. The curve B is the diagram of the case where water is added so that the amount thereof becomes 0.2 mole fraction. In this case also, the curve B intersects the diagonal line, and therefore it is understood that an azeotrope is formed. The curve C is the diagram of the case where the amount of water is 0.5 mole fraction (50 mole%). In this case, the curve C does not intersect the diagonal line and is below the diagonal line. This indicates that if more than about 50 mole% (0.5 mole fraction) of water is present in the methyl alcohol-methacrolein system, the azeotrope of methyl alcohol and methacrolein disappears and the ratio of methacrolein to methyl alcohol in the equilibrium vapor becomes significantly greater than in tbe liquid. That is, if $x_{H_2O} > 0.5$ mole fraction (50 mole%), the relative volatility of methacrolein to methyl alcohol becomes more than 1, whereby the two can be easily separated from each other. For example, when, in the curve C, $X_{MeOH}$ is 0.3, $Y_{MeOH}$ becomes 0.186. Accordingly, $X_{MAL} = 1-0.3 = 0.7$; $Y_{MAL} = 1-0.186 = 0.814$; and relative volatility ($\alpha$) : (MAL/MeOH) = $(Y_{MAL}/X_{MAL})/(Y_{MeOH}/X_{MeOH}) = (0.814/0.7)/(0.186/0.3) = 1.88$. In the some way, when, in the curve C, $X_{MeOH} = 0.7$, ($\alpha$) becomes 3.06. The curve D is the diagram of the case where the amount of water is 80 mole% ($X_{H_2O} = 0.8$), and shows that no azeotrope of methyl alcohol and methacrolein is present and the relative volatility of methacrolein to methyl alcohol becomes greater than in the case of curve C.

From the above, it will be understood that if water is made present in the methyl alcohol-methacrolein system so that the amount thereof becomes more than about 50 mole%, the azeotropic relation between methyl alcohol and methacrolein disappears and the relative volatility of methacrolein to methyl alcohol becomes more than 1 to make it possible to easily separate the two from each other.

It is not clear whether ethyl alcohol, isopropyl alcohol or normal-propyl alcohol can form an azeotrope with methacrolein. Presuming from the results of our experiments, however, it is difficult, when said alcohol is used, to separate methacrolein from said alcohol at a sufficient purity so far as an ordinary rectification operation is conducted. In other words, it is considered that the said alcohol forms an azeotrope with methacrolein, or the relative volatility thereof to methacrolein is substantially equal to 1.0. When the extractive distillation process using water as solvent is adopted, such difficulty as mentioned above can be overcome and the separation of methacrolein can be effected easily.

We have further examined whether a ternary system comprising methacrolein, an alcohol and water forms an azeotrope. If the said ternary system forms an azeotrope, it is impossible to separate methacrolein from the alcohol by subjecting the system to extractive distillation using water as solvent. This point will be mentioned below with reference to the case where the alcohol is methyl alcohol.

It is well known that a ternary system comprising acrolein, methyl alcohol and water forms an azeotrope (with boiling point 51.2°C.) composed of 85.7% by weight of acrolein, 13.4% by weight of methyl alcohol and 0.9% by weight of water. Accordingly, it is impossible to subject an acrolein-alcohol system to extractive distillation using water as solvent to separate acrolein from the alcohol. As the result of examination, however, we have experimentally confirmed that methacrolein forms no ternary components azeotrope with methyl alcohol and water. Thus, the extractive distillation according to the present invention is limited to the separation of methacrolein. It is therefore evident that the present invention which is concerned with an extractive distillation process for separation of methacrolein is entirely different from, and in unobvious from, U.S. Pat. No. 2,514,966 which is concerned with an extractive distillation process for separation of acrolein.

From our studies mentioned above, there was found the effectiveness of a process for separating methacrolein from a methacrolein-alcohol liquid by subjecting the liquid to extractive distillation using water as a solvent for varying the relative volatility between the two components, the concentration of water in the resulting liquid phase comprising methacrolein-alcohol-water ternary system in the absorbing section of extractive distillation zone being controlled to a concentration of at least 50 mole%.

With an aim to apply the said newly found extractive distillation step to a series of steps for separating methacrolein from a methacrolein-containing gaseous mixture, we made further studies and decided to utilize the knowledge that an alcohol is excellent as the absorption solvent for methacrolein. Based on this thinking, we skillfully combined the above-mentioned extractive distillation step with the step of absorbing methacrolein from a methacrolein-containing gaseous mixture by use of an alcohol solvent, and thus accomplished the present invention which can successfully accomplish the object of the present invention.

That is, the present invention provides a process or separating methacrolein from a gaseous mixture containing methacrolein which comprises:

1. absorbing the methacrolein in the gaseous mixture with an alcohol selected from the group consisting of methyl alcohol, ethyl alcohol, iso-propyl alcohol and normal-propyl alcohol, and 2. subjecting the resulting methacrolein-alcohol absorption solution to extractive distillation with water in an extractive distillation zone, wherein said solution is introduced into the middle portion of said zone and the water is caused to flow down from the upper portion of said zone so that the concentration of water in a liquid phase in an absorbing section of said zone is controlled to a concentration in the range from 50 to 90 mole%, thereby to recover the methacrolein as the top distillate of said zone and the alcohol with water as the bottom liquid of said zone.

The extractive distillation process of the present invention has such merits as mentioned below.

Since the present process employs no such methacrolein recovering and recycling step as required in the process of German Offenlegungschrift No. 2,110,031, the equipment cost is low and the troblesome operation can be dismissed.

When the amount of water added is made at least 50 mole% over the whole composition range of the methacrolein-alcohol system (i.e. regardless of the proportions of methacrolein and alcohol), methacrolein can be separated from alcohol. Accordingly, even if the methacrolein-alcohol absorption solution obtained in the step (1) contains large quantities of alcohol, methacrolein can effectively be separated from alcohol by addition of far smaller amount of water than in said German Offenlegungschrift process.

Since water is used in such a small amount as above, burdens in the subsequent distillation step for separation of alcohol from water also become far less than in said German Offenlegungschrift process.

In the present invention, the amount of water used in the extractive distillation zone is far smaller than in U.S. Pat. No. 2,514,966. Accordingly, the present process is far lower in utility cost than the United States Patent process.

The relative volatility between the two components in the methacrolein-alcohol system at the time of extractive distillation may properly be controlled by the amount of water added, so that the operation can be effected at atmospheric pressure. As the result, ordinary cooling water may be used for the condensation of methacrolein gas distilled from the extractive distillation column, whereby the increase in cooling cost can be avoided. Furthermore, the bottom of the column is brought to such a low temperature as substantially equal to the boiling point of the aqueous alcohol solution, so that the occurrence of undesirable side-reactions such as polymerization of methacrolein or dimerization thereof due to Diels-Alder reaction may be inhibited to a considerable extent.

While, in the process of the present invention, the above-mentioned extractive distillation step (2) is combined with the step of absorbing methacrolein in the gaseous mixture (1), use of the aforesaid alcohol as an absorption solvent in the step (1) gives following merit. That is, because the alcohol is not only well miscible with methacrolein as well as water, but also has a low melting point, and hence the alcohol can be cooled to such a low temperature as below 0°C. so as to be usable as a well cooled absorption solvent, and this brings about such desirable effect that a small amount of methacrolein in the gaseous mixture containing large quantities of uncondensed gases such as nitrogen, oxygen, carbon monoxide and carbon dioxide can effectively be absorbed even under such a low pressure as about 1 to 5 atm.

In case the gaseous mixture contains large quantities of steam as a diluent, there is ordinarily adopted a pre-treatment step for cooling the mixture by a suitable means and removing the condensed water. If, in this step, the loss of methacrolein is intended to be minimized as far as possible, the dehydration effect becomes insufficient in most cases. In the present invention, however, the amount of uncondensed steam entrained in the gaseous mixture entering the absorption step is not particularly required to be strictly limited, because water in the gaseous mixture entering the methacrolein absorption step is absorbed together with methacrolein by the aforesaid alcohol used as absorption solvent, and even if a more or less amount of water is present in the absorption solution, the presence of such water is not objectionable for the present process since the subsequent extractive distillation step is carried out by use of water as a solvent. This is effective to simplify the gas cooling equipment and to inhibit the loss of methacrolein by entrainment into condensed water.

It has heretofore been considered that alcohols, when used in combination with aldehydes, give rise to undesirable reactions, and hence are not preferable as solvents to be used in such cases. According to the present invention, however, it has been found that under the operational conditions of the present process, alcohols can be used without substantially injuring the stability of methacrolein. While it is not clear why such desirable effect can be obtained, it is assumed in view of the equilibrium of the system that water present in the system acts so as not to cause undesirable reactions.

The effects of the present process using the alcohol having 1 to 3 carbon atoms as mentioned above are not obtainable, when other alcohol is used. For example, an alcohol having 4 or more carbon atoms or a polyhydric alcohol has a boiling point of more than 100°C., in general, and promotes undesirable reactions of methacrolein or forms a heterogeneous system due to decrease in mutual solubility with water, and such alcohol as tert-butyl alcohol is too high in melting point to be used as the absorption solvent in the present process.

As mentioned previously, the present invention provides a process for separating methacrolein from a methacrolein-containing gaseous mixture, wherein the step of absorbing methacrolein in the gaseous mixture by use of the above-defined alcohol as an absorption solvent is continuously combined with the extractive distillation step of subjecting the absorption solution obtained in the said absorption step to extractive distillation with water to recover the methacrolein as a distillate, thereby obtaining various marked effects.

The absorption step is ordinarily carried out under such conditions as a pressure of 1 to 10 atm. and a temperature of −30° to 30°C.

In the extractive distillation step, the methacrolein is recovered as the top distillate of the extractive distillation zone and the alcohol with water (aqueous alcohol solution) as the bottom liquid of said zone. In this operation, water is caused to flow down from the upper portion of the extractive distillation zone so that the amount of water in a liquid phase comprising methacrolein, alcohol and water which is present in an absorbing section of said zone becomes at least 50 mole%, preferably from 50 to 90 mole%. The inner pressure of the system is preferably from 0.5 to 2.0 atm. Further, the column used in the extractive distillation usually has a total of 24 to 60 plates; 14 to 33 plates for the absorbing section, 10 to 24 plates for the stripping section, and 0 to 3 plates for the solvent recovering section. (Provided that in the present invention, the solvent recovering zone acts as a demister zone, because the top distillate consists of a methacrolein-water azeotrope.) Theoretically, the ratio in number of plates of absorbing section to stripping section is about 7 : 5. The reflux ratio is ordinarily 1.5 to 5.0, preferably 1.5 to 2.0.

The separation of alcohol and water from the alcohol-water solution obtained as the bottom liquid of the extractive distillation zone may be effected according to a procedure thoroughly known to those skilled in the art, e.g. ordinary distillation, azeotropic distillation using such an entrainer as benzene, trichloroethylene or isopropyl ether. In view of the fact that the dehydration is not particularly required to be strict in the present invention, the separation is easily accomplished by ordinary distillation. The thus recovered alcohol and water can be recycled to the absorption step and the extractive distillation step, respectively.

The methacrolein-containing gaseous mixture used as the feed gas in the present process is not particularly limited. When viewed from the industrial standpoint, however, a feed gas, to which the present process is effectively applicable, is a high temperature gaseous reaction mixture obtained by the vapor phase catalytic oxidation of isobutylene, an isobutylene-containing hydrocarbon mixture, e.g. a $C_4$ hydrocarbon mixture containing isobutylene, or methacrolein. A preferable gaseous mixture containing methacrolein is one which is obtained by subjecting isobutylene, an isobutylene-containing hydrocarbon mixture, e.g. a $C_4$ hydrocarbon mixture containing isobutylene, or methacrolein, to vapor phase catalytic oxidation in the presence of steam, preferably in the additional presence of nitrogen, and cooling the resulting high temperature gaseous reaction mixture to form (a) a gaseous mixture containing methacrolein and (b) a condensed liquid phase, the latter liquid phase being removed. The $C_4$ hydrocarbon mixture containing isobutylene is preferably composed mainly of isobutylene. The said gaseous mixture (a) comprises aldehydes composed mainly of methacrolein, uncondensed steam, nitrogen, oxygen, carbon monoxide, carbon dioxide, unreacted isobutylene and the like hydrocarbons. The said condensed liquid phase (b) comprises, condensed or dissolved steam and methacrylic acid (by-product or product) and slight amounts of other organic acids, aldehydes and ketones. The above-mentioned process of the present invention is advantageously applicable to the separation of methacrolein from the said gaseous mixture (a).

As mentioned previously, the present invention provides a methacrolein separation process which is commercially and economically advantageous and is characteristically applicable.

Figure 2:
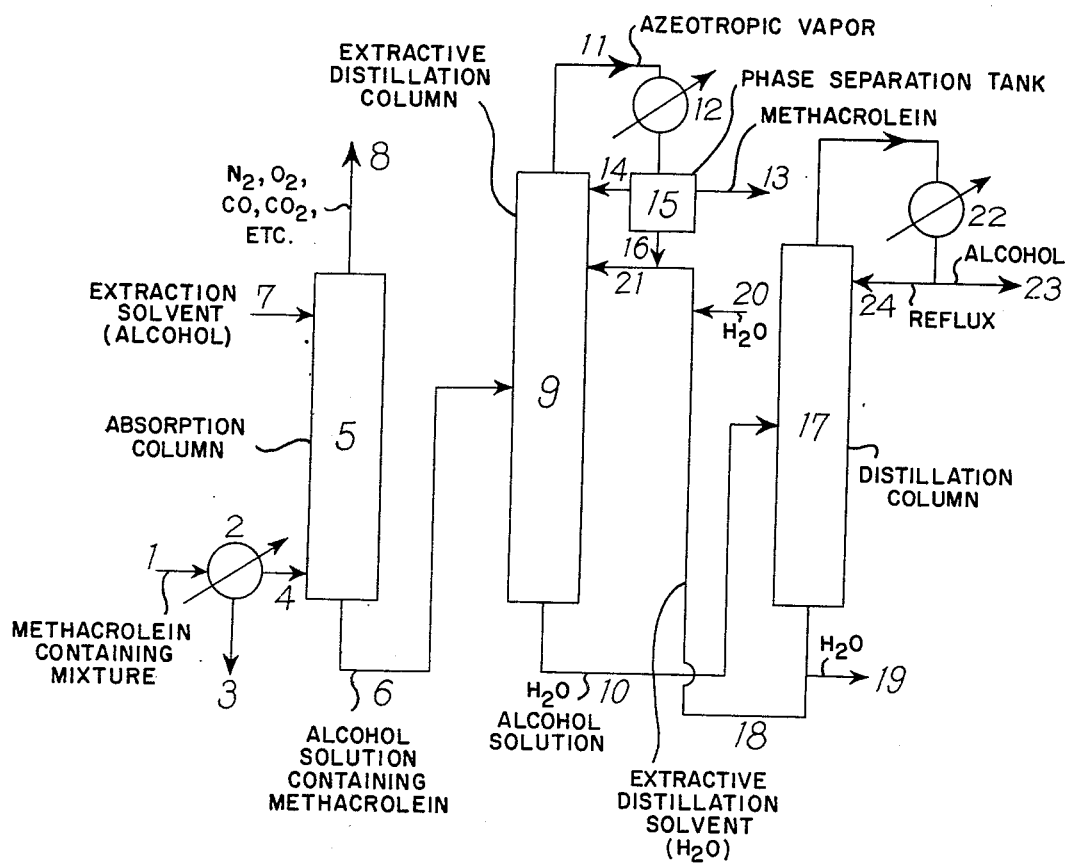

The present invention is further illustrated below with reference to the accompanying drawing FIG. 2, which is a flow sheet showing an embodiment of the invention.

In the first place, a high temperature gaseous reaction mixture 1, which has been formed by the vapor phase catalytic oxidation of isobutylene or an isobutylene-containing hydrocarbon mixture, or methacrolein in the presence of oxygen, nitrogen and steam, is cooled by a suitable cooling means, e.g. an indirect heat exchanger 2, to a temperature as low as 60°C. The resulting condensed liquid phase comprising a major proportion of the steam and methacrylic acid and the like high boilings separated, and withdrawn through a pipe 3 and, if necessary, the components dissolved therein may be recovered. The resulting gas phase (i.e. a gaseous mixture containing methacrolein) is sent, preferably at below about 60°C., through a pipe 4 to the lower part of methacrolein absorption column 5.

In the absorption column 5, the absorption of methacrolein with alcohol is effected under a pressure and at a low temperature, preferably under 1 to 10 atm. and at a temperature of from −30° to +30°C. As the absorption solvent, the solvent (alcohol) recovered from a distillation column 17 may be used, if necessary after purification. The solvent is charged in a desired amount, if necessary together with a proper amount of a polymerization inhibitor, through a pipe 7 to near the top of the absorption column 5.

The amount of the feed gaseous mixture containing methacrolein is variable within a wide range depending on the concentrations of the gaseous reaction mixture, particularly methacrolein, the pressure in the system, the temperature of the solvent and the structure of the columm. Generally however, the amount is about 500 to 20,000 liters per liter of the solvent, and it is desirable to select such operational conditions that the gaseous mixture is treated in an amount as large as possible to increase the concentration of methacrolein at the bottom of the column and to decrease the amount of solvent.

The absorption column may be any of ordinary extraction columns such as packed column and plate column.

Such components as nitrogen, oxygen, carbon monoxide, carbon dioxide, etc., which have not been absored in the absorption column 5, are withdrawn through a pipe 8, and, if necessary, recovered or wasted at the subsequent step. From the bottom of the absorption column 5, an alcohol solution containing methacrolein, is recovered through a pipe 6. If necessary, this absorption solution is subjected, before feeding to the subsequent extractive distillation column 9, to a step for removing such components as may preferably be removed, e.g. lower hydrocarbons and the like low boilings, and slight amounts of acids, polymerization products and other unknown high boilings. In the extractive distillation column 9, a feed stream of the absorption solution is introduced into the middle portion of the said column, and water as a solvent is fed from at least one solvent-feeding tray which is provided at near the top of the column and at the upper portion of the starting material feeding tray. If necessary, a part of the water solvent may previously be added to the feed stream. The amount of the solvent to be fed to the column may be determined by previously calculating the amount thereof so that the concentration of water in the liquid in an absorbing section between the starting materialfeeding tray and the solvent-feeding tray becomes at least 50 mole%, preferably 50 to 90 mole%. If necessary, the solvent may be incorporated with a proper amount of a polymerization inhibitor (e.g. hydroquinone) or the like.

A vapor, which is obtained at the column top through a pipe 11 as an azeotrope of methacrolein with water, is condensed by means of a condenser 12 and sent to a tank 15 to form an organic phase (upper layer) composed mainly of methacrolein and an aqueous phase (lower layer) composed mainly of water. A part of the organic phase is refluxed through a pipe 14 to the column, while the other part is recovered as a top distillate (methacrolein through a pipe 13. If necessary, the distillate is purified by additional distillation or the like operation. The lower aqueous phase in the column 15 is withdrawn continuously or intermittently, and preferably returned through a pipe 16 to the column so as to serve as a part of the feed solvent.

The water-alcohol solution obtained from the bottom of the extractive distillation column 9 is sent through a pipe 10 to a distillation column 17 for alcohol recovery. In the column 17, the water and the alcohol which constitute said water-alcohol solution are obtained as a bottom liquid and a top distillate, respectively. From the bottom of the column 17, a part of the water is withdrawn through a pipe 19 to inhibit such undesirable substances as polymerization products or high boilings from accumulation in the water recycle system, and is fed through a pipe 21 to the extractive distillation column column 9 after supplementing thereto a proper amount of fresh water through a pipe 20. On the other hand, the alcohol is condensed by means of a condenser 22, and a part of the condensed alcohol is returned as a reflux through a pipe 24 to the column, while the other part is withdrawn as a distillate through a pipe 23. If necessary, the distillate is purified by dehydration and used as the feed solvent in the absorption column 5.

Among the alcohols usable in the present invention, methyl alcohol forms no azeotrope with water. When methyl alcohol is used, therefore, the distillate of the distillation column 17 is not required to be additionaly dehydrated and may be used directly as the feed solvent in the absorption column 5. However, ethyl alcohol or iso- (or normal-) propyl alcohol forms an azeotrope with water. When the said alcohol is used, therefore, the distillate of the column 17 is desirably subjected to dehydration according to any of procedures which are publicly known to those skilled in the art. That is, when ethyl alcohol is used, the distillate of the column 17 may be dehydrated by distillation under reduced pressure, since it is well known than an ethyl alcohol-water azeotrope is decreased in water content when subjected to reduced pressure distillation. Moreover, the solvent to be used in the absorption column 5 is not required to have strictly been dehydrated, so that the ethyl alcohol distillate of the distillation column 17 may be recycled as it is to the absorption column 5, depending on the operational conditions of the column 17. When isopropyl alcohol is used, the distillate of the column 17 may be dehydrated by use of, for example, iso-propyl ether or benzene as an entrainer.

The present invention is illustrated in further detail below with reference to examples, in which all percentages are by weight unless otherwise specified.

EXAMPLE 1

A mixture comprising $C_4$ hydrocarbon composed mainly of isobutylene, nitrogen, oxygen and steam was subjected to vapor phase catalytic oxidation at a temperature of 450° to 530°C. in the presence of a catalyst. The resulting gaseous reaction mixture was cooled with water to about 40°C. As the result, greater portions of the steam and such high boilings as fatty acids were substantially removed as a condensed liquid phase, and the thus obtained gaseous mixture comprised 78.9 mole% of nitrogen, 8.9 mole% of oxygen, 1.2 mole% of carbon monoxide and carbon dioxide, 5.9 mole% of $C_4$ hydrocarbons (1.7 mole% of butadiene and 4.2 mole% of other $C_4$ hydrocarbons), 3.2 mole% of methacrolein, 0.1 mole% of acetaldehyde, 1.7 mole% of water, and trace amounts of acetone, acetic acid and the like by-products.

The thus obtained gaseous mixture was introduced into a methacrolein absorption column 5, and 11.2 kg/hr, per 100 m³/hr (at 40°C.) of said gaseous mixture, of methyl alcohol (containing 300 p.p.m. of hydroquinone), which had been cooled to −20°C., was fed through the top of the column to absorb the methacrolein in the gaseous mixture. The absorption column was 10 inch. in inner diameter, and has 10 bubble cap plates at the upper portion and 10 lattice type plates at the lower portion. The bottom temperature of the column was an average of +7°C., and the inner pressure of the column was an average of 2.3 atm.

The absorption solution obtained from the bottom of the absorption column was composed of 47.1% of methyl alcohol, 37.6% of methacrolein, 5.1% of water, 9.2% of $C_4$ hydrocarbons, and small amounts of acetaldehyde, acetone and high boilings. A part of the absorption solution was withdrawn at a flow rate of about 53 kg/hr, and the other part thereof was taken out of the system, cooled to −20°C., and recycled at a rate of about 200 kg/hr to the lower portion (consisting of the lattice type plates) of the absorption column. The absorption solution, which had been withdrawn at a rate of about 53 kg/hr, contained large quantities of $C_4$ hydrocarbons dissolved therein, and hence was subjected to stripping to remove the hydrocarbons. The overhead vapor fraction (2.6 m³/hr) taken from stripping column contained 0.08 mole of methacrolein per mole of the $C_4$ hydrocarbons. If necessary, this vapor fraction may be returned to the gas-inlet of the absorption column. In this example, however, said vapor fraction was not recycled but was taken out of the system.

The absorption solution, which had been freed from the $C_4$ hydrocarbons, contained 52.0% of methyl alcohol, 41.2% of methacrolein, 5.8% of water, about 100 p.p.m. of $C_4$ hydrocarbons, and trace amounts of acetaldehyde and acetone. This absorption solution (47.5 kg/hr) was subjected to extractive distillation, while feeding water (containing 100 p.p.m. of hydroquinone) as a solvent at a rate of 45 kg/hr. The extractive distillation column 9 was 10 inch. in inner diameter, and was composed of 30 plates with *two* bubble caps for each plates, in which the thirteenth plate from the bottom plate was allowed to serve as a starting material-feeding tray and the second plate from the top plate was allowed to serve as a solvent-feeding tray. The reflux ratio was 2.0.

The top vapor (= overhead vapor fraction) of the extractive distillation column was condensed to form an upper layer (organic phase) comprising 93.9% of methacrolein, 3.1% of water, 0.5% of methyl alcohol, 1.4% of acetaldehyde, 1.0% of acetone, and 0.1% of other high boilings, and a lower layer (aqueous layer) comprising 91.13% of water, 5.51% of methacrolein, 1.12% of methyl alcohol, and small amounts of acetone and acetaldehyde. The column top temperature was 63°C. A part of the upper layer was returned to the column as a reflux stream, and the remainder was withdrawn as a top distillate, at a rate of 20.5 kg/hr. Accordingly, the recovery ratio of methacrolein at the extractive distillation column was 98.3%. On the other hand, a part of the lower layer was intermittently withdrawn at an average rate of 1.07 kg/hr, and recycled to the extractive distillation column so as to be used as a part of the solvent.

The bottom liquid of the extractive distillation column contained 65.2% of water, 34.2% of methyl alcohol, 0.3% of methacrolein, and small amounts of substances which appeared to be polymerization products. The column bottom temperature was 80.0°C. In the extractive distillation column, the concentration of water in the liquid at the twentieth plate from the bottom plate was 82.5 mole%. The aqueous methyl alcohol solution obtained as the bottom liquid of the extractive distillation column was subjected to distillation to recover methyl alcohol at a purity of 98.2% which contained as impurities 1.1% of methacrolein and a small amount of water.

EXAMPLE 2

Using an extractive distillation column, which was 10 inch. in inner diameter and was composed of 30 plates with *two* bubble caps each, wherein the twelfth plate from the bottom plate was allowed to serve as a starting material-feeding tray and the second plate from the top plate was allowed to serve as a solvent-feeding tray, a binary system comprising methacrolein and iso-propyl alcohol was subjected to extractive distillation in such a manner as mentioned below.

A starting material comprising 53.9% of methacrolein and 46.1% of iso-propyl alcohol was incorporated with 300 p.p.m. of hydroquinone. 100 parts by weight of this starting material was subjected to extractive distillation using 48.9 parts by weight of water (containing 100 p.p.m. of hydroquinone) as a solvent, with a reflux ratio of 1.5. The top vapor of the column was condensed to form am organic phase and a small amount of an aqueous phase. A part of the organic phase was returned as reflux stream, and the remainder (53.8 parts by weight) composed of 97.5% of methacrolein, 2.0% of water, 0.2% of iso-propyl alcohol, and small amounts of impurities was withdrawn as a top distillate. On the other hand, the bottom liquid (95.1 parts by weight) was composed of 50.3% of water, 48.3% of isopropyl alcohol, 0.13% of methacrolein, small amounts of high boilings, and trace amounts of substances which appeared to be polymerization products.

In the extractive distillation column, the concentraation of water in the liquid at the twentieth plate from the bottom plate was 79.0 mole%. The column top and column bottom temperatures were 63.5°C. and 85.0°C., respectively, and the amount of the recovered methacrolein corresponded to 97.4% of the amount of the fed methacrolein.

For comparison, the above-mentioned binary starting material was distilled in the same manner as above, except that the water solvent was not fed. As the result, the top distillate contained 7.1% of iso-propyl alcohol, and the bottom liquid was composed of 1.0% of methacrolein, 93.9% of iso-propyl alcohol, and small amounts of high boilings which were assumed to be reaction products of methacrolein with iso-propyl alcohol and/or substances which appeared to be polymerization products of methacrolein.

EXAMPLE 3

Using a distillation apparatus comprising a glass-made Oldershaw type column of 1.5 inch, in inner diameter which was composed of 30 plates, a binary system consisting of methacrolein and ethyl alcohol was subjected to distillation. Even when the reflux ratio was increased, however, the concentration of ethyl alcohol in the top distillate of the column became 19.0 – 22.5%., and it was difficult to increase the purity of methacrolein to at least 85%.

Accordingly, extractive distillation using water as a solvent was carried out in the manner described below.

A starting material comprising 50.3% of methacrolein and 49.7% of ethyl alcohol was incorporated with 300 p.p.m. of hydroquinone. 100 parts by weight of this starting material was fed to the above-mentioned distillation column using 55.8 parts by weight of water (containing 100 p.p.m. of hydroquinone) as a solvent. In the column, the fifteenth plate from the bottom plate was allowed to serve as a starting material-feeding tray and the top plate was allowed to serve as a solvent-feeding tray. The reflux ratio was 1.5.

The thus obtained top distillate was 49.3 parts by weight in amount and was composed of 95.0% of methacrolein, 2.5% of water, 1.6% of ethyl alcohol, and small amounts of high boilings. The bottom liquid was composed of 51.4% of water, 45.7% of ethyl alcohol, 1.0% of methacrolein, small amounts of high boilings, and trace amounts of substances which appeared to be polymerization products.

The concentration of water in the liquid phase in the absorbing section was calculated to be about 75 to 80 mole%.

What we claim is:

1. A process for separating methacrolein from a gaseous mixture containing methacrolein which comprises:
   1. absorbing the methacrolein in the gaseous mixture with an alcohol selected from the group consisting of methyl alcohol, ethyl alcohol, iso-propyl alcohol and normal-propyl alcohol, and
   2. subjecting the resulting methacrolein-alcohol absorption solution to extractive distillation with water in an extractive distillation zone, wherein said solution is introduced into the middle portion of said zone and the water is caused to flow down from the upper portion of said zone so that the concentration of water in a liquid phase in an absorbing section of said zone is controlled to a concentration in the range from 50 to 90 mole%, thereby to recover the methacrolein as the top distillate of said zone and the alcohol with water as the bottom liquid of said zone and wherein said bottom liquid of the extractive distillation zone is distilled to separate the alcohol from the water.

2. A process according to claim 1, wherein said gaseous mixture containing methacrolein is obtained by subjecting isobutylene, an isobutylenecontaining hydrocarbon mixture or methacrolein to vapor phase catalytic oxidation, cooling the resulting high temperature gaseous reaction mixture to form a gaseous mixture containing methacrolein and a condensed liquid phase, and then removing the condensed liquid phase.

3. A process according to claim 1, wherein said alcohol is methyl alcohol.

4. A process according to claim 2, wherein said alcohol is methyl alcohol.

5. A process according to claim 1, wherein said alcohol is methyl alcohol.

6. A process for separating methacrolein from a high temperature gaseous reaction mixture obtained by vapor phase catalytic oxidation of isobutylene or an isobutylene-containing hydrocarbon mixture which comprises:
   1. cooling the said reaction mixture to form a gaseous mixture containing methacrolein and a condensed liquid phase, and removing the condensed liquid phase,
   2. absorbing the methacrolein in the gaseous mixture with methyl alcohol,
   3. subjecting the resulting methacrolein-methyl alcohol solution to extractive distillation with water in an extractive distillation zone, wherein said solution is introduced into the middle portion of said zone and the water is caused to flow down from the upper portion of said zone so that the concentration of water in a liquid phase in an absorbing section of said zone is controlled to a concentration in the range from 50 to 90 mole%, thereby to recover the methacrolein as the top distillate of said zone and the alcohol with water as the bottom liquid of said zone, and
   4. distilling the bottom liquid obtained in the step (3) to separate the methyl alcohol from the water and recycling the methyl alcohol to the absorption step (2).

7. A process according to claim 6, wherein a part of the water obtained in the step (4) is recycled to the extractive distillation step (3).

8. A process according to claim 2, wherein said isobutylene-containing hydrocarbon mixture is a $C_4$ hydrocarbon mixture containing isobutylene.

9. A process according to claim 6, wherein said isobutylene-containing hydrocarbon mixture is a $C_4$ hydrocarbon mixture containing isobutylene.

* * * * *